United States Patent [19]

Wright

[11] Patent Number: 4,735,948

[45] Date of Patent: Apr. 5, 1988

[54] (1H-TETRAZOL-5-YL)-2(1H)-QUINOLI-NONES AND-NAPHTHYRIDONES AND ANTIALLERGIC USE THEREOF

[75] Inventor: Terry L. Wright, Clayton, Calif.

[73] Assignee: Merrell Dow Pharmaceuticals Inc., Cincinnati, Ohio

[21] Appl. No.: 478,965

[22] Filed: Mar. 25, 1983

[51] Int. Cl.$^4$ .................. C07D 471/04; C07D 403/04; A61K 31/41
[52] U.S. Cl. ..................................... 514/299; 514/312; 546/122; 546/157
[58] Field of Search ............... 546/122, 157; 548/253; 424/258; 514/299, 312

[56] References Cited

U.S. PATENT DOCUMENTS

| | | | |
|---|---|---|---|
| 3,943,141 | 3/1976 | Ellis et al. | 546/123 |
| 3,993,656 | 11/1976 | Rooney et al. | 546/122 |
| 4,035,368 | 7/1977 | Erickson et al. | 546/122 |
| 4,350,817 | 9/1982 | Scotese et al. | 546/122 |

FOREIGN PATENT DOCUMENTS 0166533  1/1986  European Pat. Off. .

Primary Examiner—Glennon H. Hollrah
Assistant Examiner—D. B. Springer
Attorney, Agent, or Firm—John J. Kolano

[57] ABSTRACT (1H-Tetrazol-5-yl)-2(1H)-quinolones useful as antiallergic agents are described herein. The compounds are prepared by the reaction of sodium azide and ammonium chloride with an appropriate 3-cyano-2(1H)-quinolinone.

10 Claims, No Drawings

(1H-TETRAZOL-5-YL)-2(1H)-QUINOLINONES AND-NAPHTHYRIDONES AND ANTIALLERGIC USE THEREOF

The present invention is directed to a group of 2(1H)-quinolinones having a tetrazole substituent at the 3- or 4-position. More particularly, it relates to compounds having the following general formula:

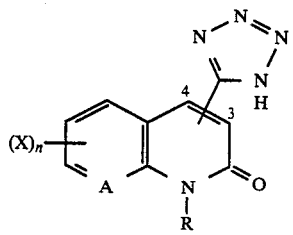

wherein A is —CH= or —N=; R is H or alkyl of 1-4C; n is 0, 1 or 2; X is H, alkyl of 1-4C, alkoxy of 1-4C, halogen, methylmercapto, methylsulfonyl, or two X's can be combined as methylenedioxy; with the proviso that, when X is methylmercapto or methylsulfonyl, then n must be 1; and the pharmaceutically acceptable salts thereof.

The substituent with the free valence entering the ring between the positions marked as 3 and 4 can only be attached to either of those two positions. The X substituent can only be attached at available 6-, 7 -and/or 8-positions in the left hand ring in the structure shown above. Halogen is fluorine, chlorine or bromine. Examples of the alkyl groups are methyl, ethyl, propyl or isopropyl; examples of the alkoxy groups are methoxy, ethoxy, propoxy, isopropoxy or butoxy.

Preferred compounds are those in which the tetrazole substituent is attached at the 3-position of the quinolinone.

Equivalent for the purposes of this invention are the pharmaceutically acceptable salts and also the hydrates of the compounds and their salts. The term "pharmaceutically acceptable salt" as used herein is intended to include non-toxic cationic salts such as the alkali metal salts, e.g., sodium and potassium; alkaline earth metal salts such as calcium, magnesium or barium; salts with ammonia; and salts with organic bases, e.g., amines such as triethylamine, n-propylamine and tri-n-butylamine.

The compounds of the present invention are prepared by the reaction of sodium azide and ammonium chloride with a cyanoquinolinone of the formula:

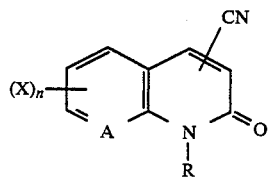

wherein n, A, R and X are defined as above. The reaction is carried out with heating in an inert solvent such as dimethylformamide. Sodium azide is the preferred azide in the reaction although other alkali metal azides can be used.

The necessary starting material is obtained from an appropriate substituted acetanilide by two different methods. In the first method, the acetanilide is heated with dimethylformamide and phosphorus oxychloride to give a 2-chloro-3-quinolinecarboxaldehyde. This particular reaction and variations thereof are discussed in detail by Meth-Cohn et al., J. Chem. Soc., Perkin Trans. 1, 1981, 1520. The carboxaldehyde is then heated with hydroxylamine hydrochloride, formic acid and sodium formate to give the corresponding 3-cyano-2(1H)-quinolinone. This provides a new and convenient method for the general synthesis of such 3-cyano-2(1H)-quinolinones and similar compounds. The new process is particularly advantageous because (1) it gives the desired product in high yield, (2) several reactions are conveniently combined in a single process, and (3) the necessary starting materials can be obtained readily. In contrast, previously described procedures for the preparation of 3-cyano-2(1H)-quinolinones involved multi-step syntheses or the use of reactants such as 2-aminobenzaldehyde which are unstable.

Alternatively, the acetanilide can be heated with dimethylformamide, phosphoryl chloride and hydroxylamine hydrochloride to give a 2-chloro-3-cyanoquinoline. This process is a particularly convenient method for obtaining the chlorocyanoquinoline directly from an acetanilide. The indicated chloro-cyano-compound can then be hydrolyzed either under acidic or basic conditions to give the corresponding desired 3-cyano-2(1H)-quinolinone. Specifically, if the 2-chloro-3-cyanoquinoline is boiled in acetic acid for 1 hour or refluxed in 4N hydrochloric acid for 10-15 minutes, the corresponding 3-cyano-2(1H)-quinolinone is obtained.

Reaction of the 3-cyano-2(1H)-quinolinones with a strong base such as potassium t-butoxide and an alkyl halide of the formula R-halogen, wherein R is defined as above and halogen is chlorine, bromine or iodine, in an appropriate solvent such as dimethylsulfoxide gives the corresponding compound having a R-substituent on the quinolinone nitrogen. Such compounds obviously serve as the starting materials for the compounds of the present invention wherein R is alkyl.

The tetrazoles of the present invention are converted to the corresponding pharmaceutically acceptable salts by reacting them with a substantially equimolar amount of the appropriate base in an aqueous solution or in a suitable organic solvent such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences, Mack Publishing Company, Easton, Pennsylvania.*

The compounds of the present invention or pharmaceutical compositions thereof may be administered to human asthmatic patients in single oral doses of approximately 1–1000 mg of active ingredient and multiple oral doses totaling up to about 4000 mg/day of active ingredient. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method
1. Antisera—Various standard methods described in the literature were used for the preparation of reaginic antisera to ovalbumin in either Hooded Lister or Brown Norway adult rats.
2. Animals—Adult male Sprague-Dawley or female Wistar Kyoto rats were used as antisera recipients in the test. The animals were allowed to acclimate for 5–14 days with food and water ad lib.
3. Sensitization—Recipient rats were passively sensitized by the intradermal injection of 100 microliters of two dilutions of antiserum (one injection on each side of the back). Sensitization occurred 48-72 hours prior to antigen challenge.
4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 240 minutes prior to challenge.
5. Antigen Challenge and Reaction Evaluation—Ovalbumin (0.1-1.0 mg in a 0.5% solution of Evan's Blue dye) in saline was given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both i.p. and orally.

In addition to activity in the PCA test as described above, the compounds of the present invention also inhibit the release of histamine in the rat Passive Peritoneal Anaphylaxis (PPA) test. This method can be described briefly as follows:

PPA Test Method
1. Antisera—Reaginic antibody to ovalbumin for this test was prepared in adult male $B_6D_2F_1$ mice.
2. Animals Adult male Sprague Dawley or female Wistar Kyoto rats were used as antibody recipients. The animals were allowed to acclimate for 5–14 days with food and water ad lib.
3. Sensitization—Recipient rats were sensitized i.p. with 2 ml of an appropriate saline dilution of the mouse anti-ovalbumin antiserum determined from prior experiments. Sensitization took place 2 hours prior to antigen challenge.
4. Administration of Test Compound—Five to ten animals were used for each test compound/dilution. Compounds were homogenized in saline with an equivalent of sodium bicarbonate to effect solubilization, if appropriate, and administered i.p. at 60 $\mu$g, 30 seconds prior to antigen challenge or p.o. 5 to 60 minutes prior to antigen challenge.
5. Antigen Challenge and Assay Evaluation—Two mg of ovalbumin in 5 ml of modified Tyrode's Solution was administered by i.p. injection and the animals were sacrificed 5 minutes later. Peritoneal shock fluids were collected and classified by centrifugation. Protein was removed from the samples by perchloric acid precipitation and subsequent centrifugation. The samples were then analyzed for histamine content by an automated fluorometric assay. Histamine levels of peritoneal shock fluids from treatment animals were then compared to those of shock fluids from control animals. Drug effect was expressed as percent inhibition of histamine release.

The following examples are presented to illustrate the present invention but they should not be construed as limiting in any way.

EXAMPLE 1

To a mixture of 11880 ml of phosphoryl chloride and 2500 g of acetanilide was added, with cooling and stirring in an ice bath, 3380 g of dimethylformamide at such a rate that the temperature did not exceed 60° C. The addition took about 45 minutes, at which time the cooling bath was removed and the mixture was heated to 75° C. for 22 hours. The mixture was then cooled and the excess phosphoryl chloride was removed by rotary evaporation. The residual dark brown oil was then poured into about 32 liters of water with stirring. Ice was added to the aqueous mixture to keep the temperature below 50° C. The dark yellow solid which formed was separated by filtration and dried in a forced-air oven at 70° C. to give 2-chloro-3-quinolinecarboxaldehyde melting at about 145°–147° C.

EXAMPLE 2

To the mixture obtained by the addition of 210 g of 4-(methylthio)acetanilide to 1246 g of phosphoryl chloride there was added 254 g of dimethylformamide over a period of 30 minutes with stirring. The reaction was exothermic and the rate of addition was controlled so that the temperature did not exceed 75° C. After the addition was complete, the reaction was heated at 75° C. for 2.5 hours. The mixture was then quenched in water and the yellow precipitate which formed was separated by filtration and dried to give 2-chloro-6-methylthio-3-quinolinecarboxaldehyde.

When the above procedure was repeated using the appropriate substituted acetanilide, the following products were obtained:
  2-Chloro-6,7-dimethoxy-3-quinolinecarboxaldehyde.
  2,6-Dichloro-3-quinolinecarboxaldehyde.
  2-Chloro-7-methylthioquinolinecarboxaldehyde.

EXAMPLE 3

A mixture was prepared from 6 liters of 97% formic acid, 300 g of hydroxylamine hydrochloride, 500 g of sodium formate, and 700 g of 2-chloro-3-quinolinecarboxaldehyde and this mixture was heated to reflux (110° C.). The resulting solution was then maintained at 110° C. for 18 hours. The solution was then cooled and the solid which crystallized was separated by filtration and then successively washed twice with water, once with ethanol and once with methylene chloride to give 3-cyano-2(1H)-quinolinone.

EXAMPLE 4

A mixture was prepared from 15 g of 2-chloro-6,7-dimethyl-3-quinolinecarboxaldehyde, 5.4 g of hydroxylamine hydrochloride, 8.5 g of sodium formate and 155 ml of 97% formic acid and this was heated at reflux for 3 hours. Initially, the mixture became a heavy yellow paste but a homogeneous brown solution formed later. However, by the end of the 3-hour reflux period, the mixture was again heterogeneous and it was cooled and poured into 300 ml of water. The solid which formed was separated by filtration and dried to give 3-cyano-6,7-dimethyl-2(1H)-quinolinone melting at about 300° C. The indicated product contained ¼ molecule of water of hydration.

When the above procedure was repeated using the appropriate starting materials, the following compounds were obtained:
  3-Cyano-6,7-dimethoxy-2(1H)-quinolinone (¼ H$_2$O) melting at greater than 300° C.
  3-Cyano-6-methylthio-2(1H)-quinolinone (1/6 H$_2$O) melting at about 287°–288° C.
  6-Chloro-3-cyano-2(1H)-quinolinone.
  3-Cyano-7-methylthio-2(1H)-quinolinone

EXAMPLE 5

To a solution of 10 ml of 30% hydrogen peroxide and 100 ml of acetic acid there was added 4.0 g of 3-cyano-6-methylthio-2(1H)-quinolinone and the mixture was heated at reflux for 1.5 hours. A homogeneous solution formed initially but, during the course of the reaction, a light yellow precipitate appeared. The mixture was cooled and the solid was separated by filtration to give 3-cyano-6-methylsulfonyl-2(1H)quinolinone melting at greater than 310° C. When the procedure described above was repeated using 3-cyano-7-methylthio-2(1H)-quinolinone, the product obtained was 3-cyano-7-methylsulfonyl-2(1H)-quinolinone.

EXAMPLE 6

To a mixture of 118 ml of phosphoryl chloride and 5 g of acetanilide was added, with cooling and stirring in an ice bath, 41 g of dimethylformamide at such a rate that the temperature did not exceed 75° C. After the addition was complete, a heat lamp was applied and the temperature was maintained at 75° C for 20 hours. Heating was then stopped and the mixture was allowed to cool for a few minutes and the temperature fell to 62° C. Hydroxylamine hydrochloride (14 g) was added all at once to the stirred mixture. After about 2–3 minutes, a slow exothermic reaction started and the mixture began to boil with considerable gas evolution. The temperature rose slowly from 62° C to 77° C over a period of about 15 minutes. By this time, gas evolution had almost stopped. The mixture was then allowed to cool to room temperature and a heavy yellow solid precipitated. The mixture was then quenched carefully by the addition of 1000 ml of water with vigorous stirring. The solid was then separated by filtration and dissolved in methylene chloride and the methylene chloride solution was treated with charcoal filtered, concentrated and cooled. Filtration then gave light yellow crystals of 2-chloro-3-cyanoquinoline.

EXAMPLE 7

A mixture was prepared by adding 5.0 g of 3-cyano-2(1H)-quinolinone, 10 g of potassium t-butoxide and 4.6 g of methyl iodide to 50 ml of dimethylsulfoxide and the mixture was heated at 80° C for 3 hours. A dark homogeneous solution resulted. This was cooled and poured into water and the aqueous mixture was extracted with methylene chloride. The organic extract was then treated with silica gel and filtered and the filtrate was concentrated until crystallization occurred. This gave 3-cyano-1-methyl-2(1H)-quinolinone melting at about 202°–205° C.

EXAMPLE 8

To a solution of 250 g of 3-cyano-2(1H)-quinolinone in 3000 ml of dimethylformamide was added 86.5 g of ammonium chloride and 105 g of sodium azide. The stirred heterogeneous solution was heated at 110° C. for 17 hours. The mixture was then cooled and poured into 8 liters of water and acidified to pH 2 with concentrated hydrochloric acid under vigorous stirring. The precipitate which formed was separated by filtration, washed with water and dried in vacuo. The crude product was recrystallized from hot dimethylformamide wherein water was added to the hot solution until precipitation began and the mixture was then cooled to room temperature. The solid obtained in this way was 3-(1H-tetrazol-5-yl)-2(1H)-quinolinone.

This compound has the following structural formula:

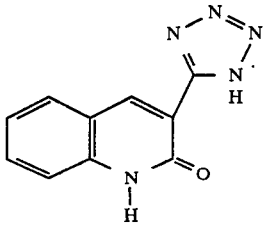

EXAMPLE 9

A suspension of 690 g of the product obtained in the preceding example in 8 liters of 50% aqueous ethanol was heated to 70° C. A solution of 136 g of sodium hydroxide in 500 ml of water was added to the stirred solution over a period of 10 minutes. The original solid dissolved almost completely and, after several minutes, a heavy precipitate formed. The mixture was then allowed to cool and the solid was separated by filtration to give the sodium salt of 3-(1H-tetrazol-5-yl)-2(1H)-quinolinone.

EXAMPLE 10

A mixture of 5.0 g of 3-cyano-2(1H)-quinolinone, 1.9 g of ammonium chloride and 2.4 g of sodium azide in 50 ml of dimethylformamide was heated at 120° C for 16 hours. The mixture was then poured into 250 ml of water and the resulting mixture was acidified to pH 2 with concentrated hydrochloric acid. The solid which formed was separated by filtration and dried. It was then dissolved in aqueous sodium hydroxide and the aqueous solution was washed with methylene chloride and filtered and the filtrate was acidified with hydrochloric acid. The light tan solid which formed was separated by filtration and dried to give 3-(IH-tetrazol-5-yl)-2(1H)-quinolinone 1/9 hydrate melting at about 301°-303° C. with decomposition.

EXAMPLE 11

When the procedure of the preceding example was repeated using the appropriate substituted 3-cyano-2-(1H)-quinolinone, the following compounds were obtained:

6,7-Dimethyl-3-(1H-tetrazol-5-yl)-2(1H)-quinolinone hemihydrate melting at about 316°-318° C. with decomposition.

6-Chloro-3-(1H-tetrazol-5-yl)-2(1H)-quinolinone, solvate with dimethylsulfoxide, melting at above 300° C.

6-Methylsulfonyl-3-(1H-tetrazol-5-yl)-2(1H)-quinolinone tetartohydrate melting at greater than 300° C.

1-Methyl-3-(1H-tetrazol-5-yl)-2(1H)-quinolinone melting at about 302°-303° C. with decomposition.

7-Methylthio-3-(1H-tetrazol-5-yl)-2(1H)-quinolinone melting at above 300° C.

7-Methylsulfonyl-3-(1H-tetrazol-5-yl)-2(1H)-quinolinone melting above 300° C.

6,7-Dimethoxy-3-(1H-tetrazol-5-yl)-2(1H)-quinolinone is also obtained from the appropriate cyano compound.

EXAMPLE 12

A solution was prepared by heating 6.0 parts of 3-cyano-2(1H)naphthyridinone in 150 ml of dimethylformamide. There was then added 1.9 g of ammonium chloride and 2.3 g of sodium azide and the resulting solution was heated at 120° C. for 84 hours. The mixture was then poured into 500 ml of water and acidified to pH 2 with concentrated hydrochloric acid. The light yellow precipitate which formed was separated by filtration, washed with water and dried to give 3-(1H-tetrazol-5-yl)-2(1H)-naphthyridinone (⅓ hydrochloride) melting at greater than 300° C.

What is claimed is:

1. A compound of the formula:

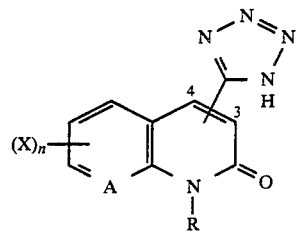

wherein A is —CH= or —N=; R is H or alkyl of 1-4C; n is 0, 1 or 2; X is H, alkyl of 1-4C, alkoxy of 1-4C, halogen, methylmercapto, methylsulfonyl, or two X's can be combined as methylenedioxy; with the proviso that, when X is methylmercapto or methylsulfonyl, then n must be 1; and the pharmaceutically acceptable salts thereof.

2. A compound according to claim 1 having the following formula:

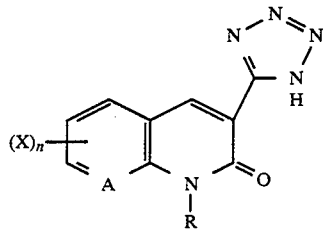

wherein A is —CH= or —N=; R is H or alkyl of 1-4C; n is 0, 1 or 2; X is H, alkyl of 1-4C, alkoxy of 1-4C, halogen, methylmercapto, methylsulfonyl, or two X's can be combined as methylenedioxy; with the proviso that, when X is methylmercapto or methylsulfonyl, then n must be 1; and the pharmaceutically acceptable salts thereof.

3. A compound according to claim 1 having the formula:

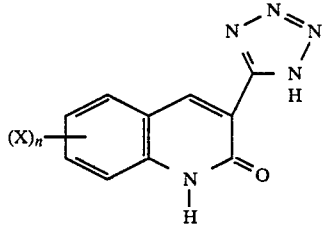

wherein n is 0, 1 or 2; X is hydrogen, alkyl of 1-4C, alkoxy of 1-4C, halogen, methylmercapto, methylsulfonyl, or two X's can be combined as methylenedioxy; with the proviso that, when X is methylmercapto or methylsulfonyl, then n must be 1; and the pharmaceutically acceptable salts thereof.

4. A compound according to claim 1 which is 3-(1H-tetrazol-5-yl)-2(1H)-quinolinone and the pharmaceutically acceptable salts thereof.

5. A compound according to claim 1 which is 3-(1H-tetrazol-5-yl)-2(1H)-quinolinone.

6. A compound according to claim 1 which is the sodium salt of 3-(1H-tetrazol-5-yl)-2(1H)-quinolinone.

7. A compound according to claim 1 which is 1-methyl-3-(1H-tetrazol-5-yl)-2(1H)-quinolinone.

8. A compound according to claim 1 which is 3-(1H)-tetrazol-5-yl)-2(1H)-naphthyridinone.

9. A method for inhibiting the results of antibody-antigen reactions in mammals which comprises administration to a mammal susceptible to allergic reaction of an effective amount of a compound of the formula:

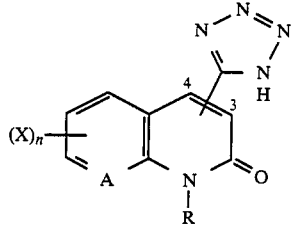

wherein A is —CH= or —N=; R is H or alkyl of 1-4C; n is 0, 1 or 2; X is H, alkyl of 1-4C, alkoxy of 1-4C, halogen, methylmercapto, methylsulfonyl, or two X's can be combined as methylenedioxy; with the proviso that, when X is methylmercapto or methylsulfonyl, then n must be 1; and the pharmaceutically acceptable salts thereof.

10. A method according to claim 9 which comprises administration of an effective amount of 3-(1H-tetrazol-5-yl)-2(1H)-quinolinone.

* * * * *

UNITED STATES PATENT AND TRADEMARK OFFICE
CERTIFICATE OF CORRECTION

PATENT NO. : 4,735,948

DATED : April 5, 1988

INVENTOR(S) : Terry L. Wright

It is certified that error appears in the above-identified patent and that said Letters Patent are hereby corrected as shown below:

On the title page, item [54], "NONES AND-NAPHTHYRIDONES AND" should read -- NONES AND NAPHTHYRIDONES AND --.

Column 6, line 12, "5" should read -- 25 --.

Signed and Sealed this

Twenty-first Day of February, 1989

Attest:

DONALD J. QUIGG

*Attesting Officer*  *Commissioner of Patents and Trademarks*